(12) United States Patent
Parchani et al.

(10) Patent No.: US 11,751,772 B2
(45) Date of Patent: Sep. 12, 2023

(54) SYSTEM AND A METHOD FOR MYOCARDIAL PERFORMANCE DETERMINATION

(71) Applicant: Turtle Shell Technologies Private Limited, Bengaluru (IN)

(72) Inventors: Gaurav Parchani, Bengaluru (IN); Mudit Dandwate, Bengaluru (IN)

(73) Assignee: Turtle Shell Technologies Private Limited

( * ) Notice: Subject to any disclaimer, the term of this patent is extended or adjusted under 35 U.S.C. 154(b) by 373 days.

(21) Appl. No.: 17/081,369

(22) Filed: Oct. 27, 2020

(65) Prior Publication Data
US 2021/0127983 A1    May 6, 2021

(30) Foreign Application Priority Data
Oct. 31, 2019    (IN) .............................. 201941044124

(51) Int. Cl.
*A61B 5/024*    (2006.01)
*G16H 50/30*    (2018.01)
(Continued)

(52) U.S. Cl.
CPC .......... *A61B 5/024* (2013.01); *A61B 5/02028* (2013.01); *A61B 5/7225* (2013.01);
(Continued)

(58) Field of Classification Search
CPC ... A61B 5/024; A61B 5/02028; A61B 5/7225; A61B 5/7257; A61B 5/7264;
(Continued)

(56) References Cited

U.S. PATENT DOCUMENTS 7,846,104 B2    12/2010    MacQuarrie et al.
9,026,202 B2    5/2015    Mbert
(Continued)

FOREIGN PATENT DOCUMENTS

CN    107960990 A    4/2018
CN    109411041 A  *  3/2019    .......... A61B 5/0006
(Continued)

OTHER PUBLICATIONS

"Te-Ming Huang et al., Kernel Based Algorithms for Mining Huge Data Sets, 2006, Springer, 1860-949X" (Year: 2006).*
(Continued)

*Primary Examiner* — Carl H Layno
*Assistant Examiner* — Aya Ziad Bakkar
(74) *Attorney, Agent, or Firm* — Lerner David LLP

(57) ABSTRACT

A system and method for myocardial performance determination is provided. The present invention provided for generating a first dataset representing a set of events associated with a pre-defined parameter of a biomarker extracted from physiological parameters of a subject. The set of events is determined by processing the pre-defined parameter at a first level and a second level of a multi-level artificial neural network architecture recursively for a pre-defined number of times. Further, generating second dataset representing characteristics associated with the set of events by processing first dataset at third level and fourth level of multi-level artificial neural network architecture. Further, computing set of values associated with set of events by processing second dataset at fifth level of multi-level artificial neural network architecture. Further, computing myocardial performance index based on set of values. The myocardial performance index is representative of myocardial performance of the subject.

23 Claims, 11 Drawing Sheets

(51) Int. Cl.
  *G16H 50/20* (2018.01)
  *A61B 5/02* (2006.01)
  *A61B 5/00* (2006.01)
  *G16H 40/67* (2018.01)
  *G16H 50/70* (2018.01)

(52) U.S. Cl.
  CPC .......... *A61B 5/7257* (2013.01); *A61B 5/7264* (2013.01); *G16H 40/67* (2018.01); *G16H 50/20* (2018.01); *G16H 50/30* (2018.01); *G16H 50/70* (2018.01)

(58) Field of Classification Search
  CPC ........ G16H 40/67; G16H 50/30; G16H 50/70; G16H 50/20; G06N 3/02
  See application file for complete search history.

(56) References Cited

U.S. PATENT DOCUMENTS

| 9,700,219 | B2 | | 7/2017 | Sharma et al. | |
| 10,441,185 | B2 | * | 10/2019 | Rogers | A61B 5/4875 |
| 2017/0347899 | A1 | * | 12/2017 | Bhushan | A61B 8/42 |
| 2018/0108440 | A1 | * | 4/2018 | Stevens | G06N 3/0445 |

FOREIGN PATENT DOCUMENTS

| KR | 20160053718 A | 5/2016 |
| WO | 2017140748 A2 | 8/2017 |

OTHER PUBLICATIONS

"Tor et al., Cardiac Time Intervals Measured by Tissue Doppler Imaging M-mode: Association With Hypertension, Left Ventricular Geometry, and Future Ischemic Cardiovascular Diseases, 2016, American Heart Association" (Year: 2016).*

Lu, H., et al., "A Novel Deep Learning based Neural Network for Heartbeat Detection in Ballistocardiograph." Annu Int Conf IEEE Eng Med Biol Soc., Jul. 2018, pp. 2563-2566.

* cited by examiner

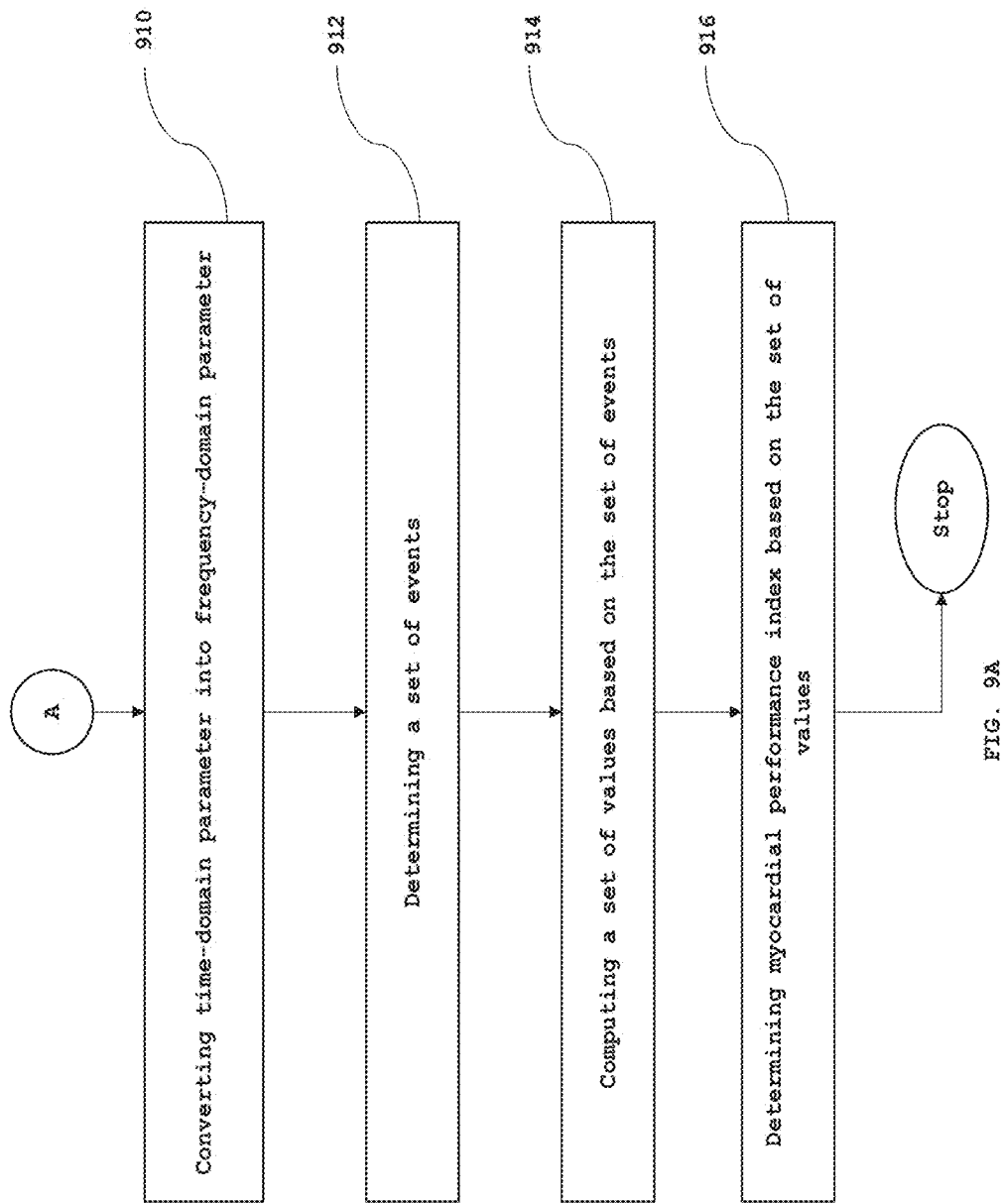

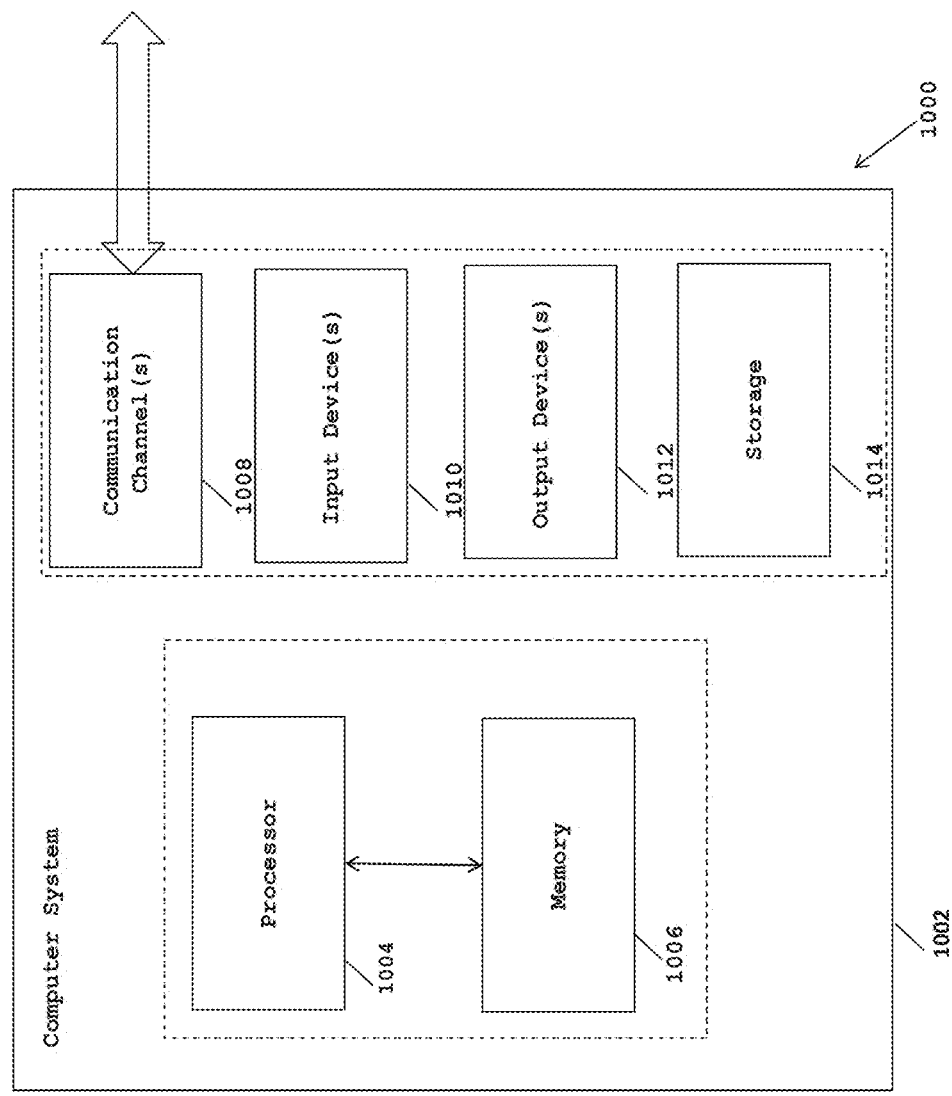

SYSTEM AND A METHOD FOR MYOCARDIAL PERFORMANCE DETERMINATION

FIELD OF THE INVENTION

The present invention relates generally to the field of monitoring a person's physiological parameters. More particularly, the present invention relates to a system and a method for contactless monitoring of cardiac activity for myocardial performance determination.

BACKGROUND OF THE INVENTION

Health monitoring has become a prerequisite in today's age of stressful and busy lifestyle. Health monitoring requires monitoring a person's physiological parameters such as, heart rate, blood pressure, body temperature etc. Health monitoring aids in determining the state of a person's body for timely detection and treatment of a disease. One of the most essential physiological parameters, which needs to be regularly monitored, is cardiac health, for prevention of cardiovascular diseases and sudden heart failures or heart attacks. People usually do not have time to visit a physician for regular cardiac health check-ups or may ignore regular cardiac check-ups, which may lead to delay in detection of cardiovascular diseases and the undetected cardiac anomalies may affect the person fatally. Further, usually experts, such as physicians, are needed in order to monitor his/her cardiac health.

Conventional techniques applied for cardiac health monitoring requires a person to be present at a particular location, such as a hospital or a clinic, and a person is not able to access such equipment regularly. Further, such equipment operate in an obtrusive manner (e.g. electrodes based electrocardiograph etc.) and are bulky in size. Furthermore, such obtrusive cardiac health monitoring may cause discomfort to the person. Existing systems, therefore, provide for cardiac health monitoring at a particular point of time, at a particular location and not regularly as such equipment are not portable and are expensive. Furthermore, such equipment are typically utilized only when the person show symptoms of cardiovascular diseases etc. and are not utilized as a preventive measure for healthy persons.

In light of the aforementioned drawbacks, there is a need for a system and a method which efficiently monitors and detects a person's cardiac activity in a contactless manner and with minimum human intervention. There is a need for a system and a method for regular monitoring of a person's cardiac health with enhanced precision and accuracy. Further, there is a need for a system and a method for monitoring cardiac activity of not only a person with cardiac disease history, but for a healthy person as a preventive measure. Furthermore, there is a need for a system and a method for cardiac activity monitoring which is easily deployable, easily implementable and cost effective.

SUMMARY OF THE INVENTION

In various embodiments of the present invention, a system for myocardial performance determination is provided. The system comprises a memory storing program instructions, a processor configured to execute the instructions stored in the memory and a computation engine executed by the processor. The computation engine is configured to generate a first dataset representing a set of events associated with a pre-defined parameter of a biomarker extracted from physiological parameters of a subject. The set of events is determined by processing the pre-defined parameter at a first level and a second level of a multi-level artificial neural network architecture recursively for a pre-defined number of times. The computation engine generates a second dataset representing characteristics associated with the set of events by processing the first dataset at a third level and a fourth level of the multi-level artificial neural network architecture. Further, the computation engine computes a set of values associated with the set of events by processing the second dataset at a fifth level of the multi-level artificial neural network architecture. Lastly, the computation engine computes a myocardial performance index based on the set of values. The myocardial performance index is representative of the myocardial performance of the subject.

In various embodiments of the present invention, a method for myocardial performance determination is provided. The method comprises generating, by a processor, a first dataset representing a set of events associated with a pre-defined parameter of a biomarker extracted from physiological parameters of a subject. The set of events is determined by processing the pre-defined parameter at a first level and a second level of a multi-level artificial neural network architecture recursively for a pre-defined number of times. The method further comprises generating, by the processor, a second dataset representing characteristics associated with the set of events by processing the first dataset at a third level and a fourth level of the multi-level artificial neural network architecture. The method further comprises computing, by the processor, a set of values associated with the set of events by processing the second dataset at a fifth level of the multi-level artificial neural network architecture. The method further comprises computing, by the processor, a myocardial performance index based on the set of values. The myocardial performance index is representative of the myocardial performance of the subject.

BRIEF DESCRIPTION OF THE ACCOMPANYING DRAWINGS

The present invention is described by way of embodiments illustrated in the accompanying drawings wherein:

FIG. 9 and FIG. 9A illustrates a flowchart of a method for contactless monitoring of cardiac activity for myocardial performance determination, in accordance with various embodiments of the present invention; and FIG. 10 illustrates an exemplary computer system in which various embodiments of the present invention may be implemented.

DETAILED DESCRIPTION OF THE INVENTION

The present invention discloses a system and a method for contactless monitoring of cardiac activity for myocardial performance determination. In particular, the present invention discloses a system and a method for contactless monitoring of cardiac activity for myocardial performance determination based on computation of myocardial performance index (MPI) associated with heartbeats of a subject. The present invention provides for a system and a method for cardiac activity monitoring and detection with precision and accuracy without the need of a physician. The present invention provides for a system and a method for MPI computation based on detection of ballistocardiographic (BCG) signals associated with a person or a subject. The present invention further provides for a system and a method with in-built intelligent mechanism for myocardial performance index (MPI) computation based on artificial intelligence techniques and machine learning techniques. The present invention provides for a system and a method for detection of myocardial performance indicators in an unobtrusive manner. Further, the present invention provides for a system and a method for regular and effective monitoring of a person's cardiac health. Furthermore, the present invention provides for a preemptive system and a method for monitoring cardiac activity of not only a person with cardiac disease history, but for a healthy person as a preventive measure. Furthermore, the present invention provides for a system and a method which is easily deployable, easily implementable, easily portable and cost effective.

The disclosure is provided in order to enable a person having ordinary skill in the art to practice the invention. Exemplary embodiments herein are provided only for illustrative purposes and various modifications will be readily apparent to persons skilled in the art. The general principles defined herein may be applied to other embodiments and applications without departing from the spirit and scope of the invention. The terminology and phraseology used herein is for the purpose of describing exemplary embodiments and should not be considered limiting. Thus, the present invention is to be accorded the widest scope encompassing numerous alternatives, modifications and equivalents consistent with the principles and features disclosed herein. For purposes of clarity, details relating to technical material that is known in the technical fields related to the invention have been briefly described or omitted so as not to unnecessarily obscure the present invention.

The present invention would now be discussed in context of embodiments as illustrated in the accompanying drawings.

Figure 1:
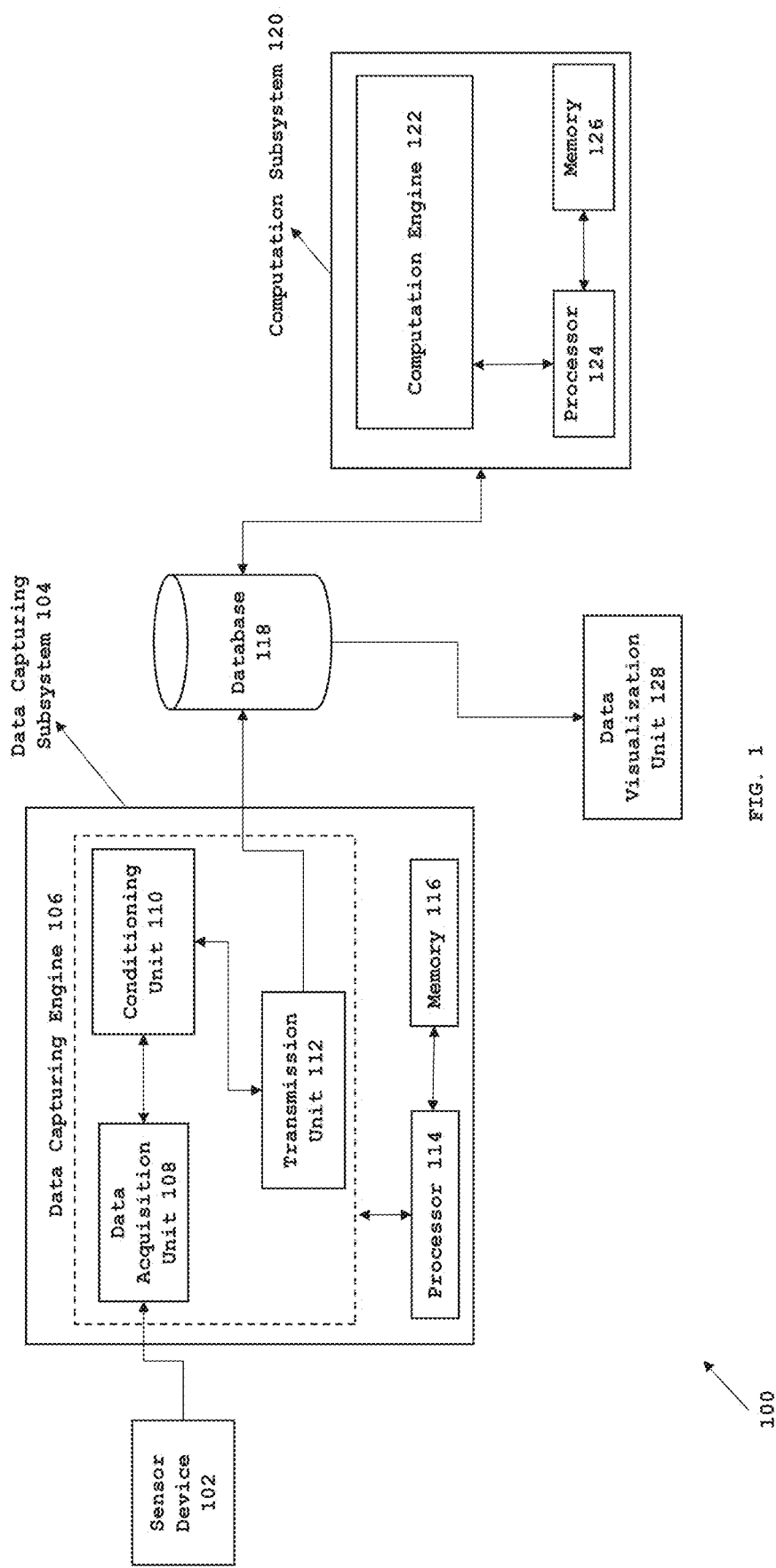
FIG. 1 illustrates a block diagram of a system for contactless monitoring of cardiac activity myocardial performance determination, in accordance with an embodiment of the present invention.

FIG. 1 illustrates a block diagram of a system 100 for contactless monitoring of cardiac activity for myocardial performance determination, in accordance with various embodiments of the present invention.

In an embodiment of the present invention, the system 100 comprises a sensor device 102, a data capturing subsystem 104, a database 118, a computation subsystem 120 and a data visualization unit 128.

Figure 3:
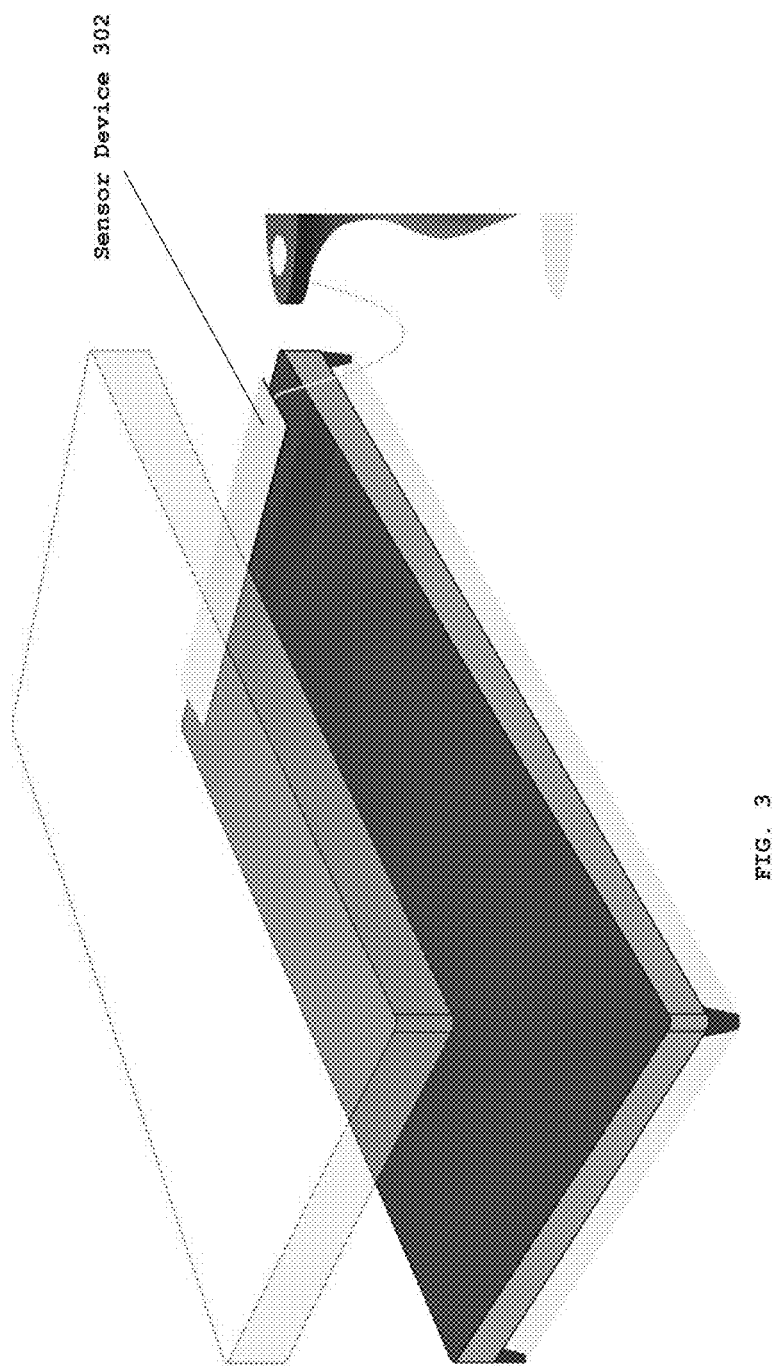
FIG. 3 illustrates placement of a sensor device, in accordance with an embodiment of the present invention.

In an embodiment of the present invention, the sensor device 102 comprises an array of sensors which are placed in a housing at the person's or subject's end. The sensor device 102 is specifically designed for carrying out various embodiments of the present invention. In an exemplary embodiment of the present invention, the sensor device 102 is of a very low thickness, preferably of around 3 mm and has an outer casing for protecting and covering the housing. The outer casing may be a robust and rugged thin cover made of a material, but is not limited to, a mesh, latex, cloth, polymer etc. that firmly holds the array of sensors in a fixed position. In another exemplary embodiment of the present invention, the sensor device 102 comprises, vibroacoustic sensors, piezoelectric sensors etc. The sensor device 102 may be of particular shapes and sizes that may include, but is not limited to, rectangular, square, circular, oval etc. The sensor device 102 is capable of being folded and is a lightweight device. In various embodiments of the present invention, the sensor device 102 is used in a non-invasive and contactless manner. The sensor device 102 may be placed under a medium such as a mattress, cushion etc., as illustrated in FIG. 3, on which a subject may sit, lie down or sleep. The sensor device 102 may be aligned in any resting position such as, but is not limited to, sitting position, lying down position etc. with respect to the subject.

In an embodiment of the present invention, in operation, the sensor device 102, positioned in a contactless manner at the subject's end, is configured to capture micro-vibrations corresponding to physiological parameters of the subject as analog data signals. The sensor device 102 is capable of capturing micro-vibrations received through a medium placed between the subject and sensor device 102. For example, the micro-vibrations may be captured through a medium ranging from a thin surface to a thick surface such as a 20-inch mattress. The micro-vibrations captured by the sensor device 102 may include, but are not limited to, ballistocardiographic (BCG) signals associated with physiological parameters of the subject such as cardiac cycles or heart rates, heart movements, chest movements, body movements, respiration signals etc. Further, the sensor device 102 is configured to convert the captured micro-vibrations, which are analog signals, into micro-voltage digital signals. The micro-voltage digital signals may be in the range of between 0 V-3.3 V.

In an embodiment of the present invention, the data capturing subsystem 104 is configured to receive the micro-voltage digital signals from the sensor device 102 corresponding to the physiological parameters of the subject. The sensor device 102 may be connected to the data capturing subsystem 104 via a wired or wireless connection. The data capturing subsystem 104 may be positioned at the subject's location. In various embodiments of the present invention, the data capturing subsystem 104 comprises a data capturing engine 106, a processor 114 and a memory 116. The data capturing engine 106 comprises multiple units that operate in conjunction with each other for capturing and transmitting the data received from the sensor device 102 to the database 118. The various units of the data capturing engine 106 are operated via the processor 114 specifically programmed to execute instructions stored in the memory 116 for executing respective functionalities of the units of the engine 106 in accordance with various embodiments of the present invention.

In an embodiment of the present invention, the data capturing engine 106 comprises a data acquisition unit 108, a conditioning unit 110 and a transmission unit 112. In an embodiment of the present invention, the data acquisition unit 108 of the data capturing engine 106 is configured to receive the micro-voltage digital signals from the sensor device 102 and record the received micro-voltage digital signal in a pre-defined data recording format. The pre-defined data recording format may include, but is not limited to, a chronological order format.

In an embodiment of the present invention, the data acquisition unit 108 transmits the recorded micro-voltage digital signal to the conditioning unit 110. The conditioning unit 110 is configured to amplify the micro-voltage digital signals for maximizing resolution of the micro-voltage digital signals, as desired, to accurately process the micro-voltage digital signals for efficient detection of subject's physiological parameters. The maximization of resolution of micro-voltages digital signal is carried out without data loss or information loss that may occur due to clipping. Advantageously, amplification and resolution maximization of the micro-voltage digital signal aids the sensor device 102 to operate with any thickness and construction of medium between the sensor device 102 and the subject. The conditioning unit 110 is configured with multiple amplification capabilities for amplifying the micro-voltage digital signal depending upon the strength of the received micro-voltage digital signals from the data acquisition unit 108. In an exemplary embodiment of the present invention, the multiple amplification capabilities embedded in the conditioning unit 110 provides, but are not limited to, eight different amplification options that amplify the micro-voltages between the range of 15× to 2500×. The conditioning unit 110 is configured to automatically calibrate and select the amplification option. The conditioning unit 110 is based on a sensitivity shifting mechanism for automatically calibrating and selecting the amplification option. The sensitivity shifting mechanism depends upon the level of strength of the micro-voltage digital signals received from the sensor device 102.

In an embodiment of the present invention, the transmission unit 112 of the data capturing engine 106 is configured to transmit the amplified micro-voltage digital signal to the database 118. The amplified micro-voltage digital signal is transmitted to the database 118 via a communication channel (not shown). The communication channel (not shown) may include, but is not limited to, a wire or a logical connection over a multiplexed medium, such as, a radio channel in telecommunications and computer networking. Examples of telecommunications and computer networking may include a local area network (LAN), a metropolitan area network (MAN), a wide area network (WAN) or any wired or wireless network, such as, but is not limited to, Wi-Fi, Bluetooth Classic, Bluetooth Low Energy etc. In an exemplary embodiment of the present invention, the database 118 may be positioned at the location of the sensor device 102 and the data capturing subsystem 104. For example, the database 118 may be installed on a smartphone, tablet, laptop, computer system etc. of the subject. In another exemplary embodiment of the present invention, the database 118 may be positioned at a location remote to the sensor device 102 and the data capturing subsystem 104, such as, in a cloud based server. In an embodiment of the present invention, the database 118 is configured to store the micro-voltage digital signal in a pre-defined data storage format which may include, but is not limited to, one or more datasets in a chronological order format in the form of micro-voltage digital datasets.

In an embodiment of the present invention, the database 118 is configured to transmit the stored micro-voltage digital datasets corresponding to physiological parameters of the subject, to the computation subsystem 120. The computation subsystem 120 is an intelligent and self-learning subsystem configured to automatically analyze complex data relating to physiological parameters of the subject from the micro-voltage digital datasets. The physiological parameters data may comprise heartbeats (cardiac cycles), breathing rate, body movements etc. Further, the computation subsystem 120 extracts a particular pre-defined physiological parameter from the multiple physiological parameters and computes data associated with the extracted physiological parameter based on the micro-voltage digital datasets for determining myocardial performance of the subject. The extracted physiological parameter is referred to as a biomarker herein after. In an exemplary embodiment of the present invention, the extracted biomarker is a cardiac cycle and the data associated with the cardiac cycle includes a parameter associated with each cardiac cycle, a set of events associated with the parameters and values associated with the events for computing myocardial performance index to determine myocardial performance of the subject. In an exemplary embodiment of the present invention, the myocardial performance is determined by utilizing one or more of the cognitive computing techniques. The cognitive computing techniques may include, but are not limited to, artificial intelligence, machine learning, deep learning and pattern recognition technique. In an exemplary embodiment of the present invention, the computation subsystem 120 may be positioned at a location of the sensor device 102 and the data capturing subsystem 104, for example, the computation subsystem 120 may be installed in a smartphone, tablet, laptop, computer system etc. of the subject. In another exemplary embodiment of the present invention, the computation subsystem 120 may be positioned at a location remote to the sensor device 102 and the data capturing subsystem 104, such as, in a cloud based server.

In an embodiment of the present invention, the computation subsystem 120 comprises a computation engine 122, a processor 124 and a memory 126. The computation engine 122 comprises various units which work in conjunction with each other for efficiently identifying various physiological parameters from the micro-voltage digital datasets. The various units of the engine 122 are operated via the processor 124 specifically programmed to execute instructions stored in the memory 126 for executing respective functionalities of the computation engine 122 in accordance with various embodiments of the present invention.

Figure 2:
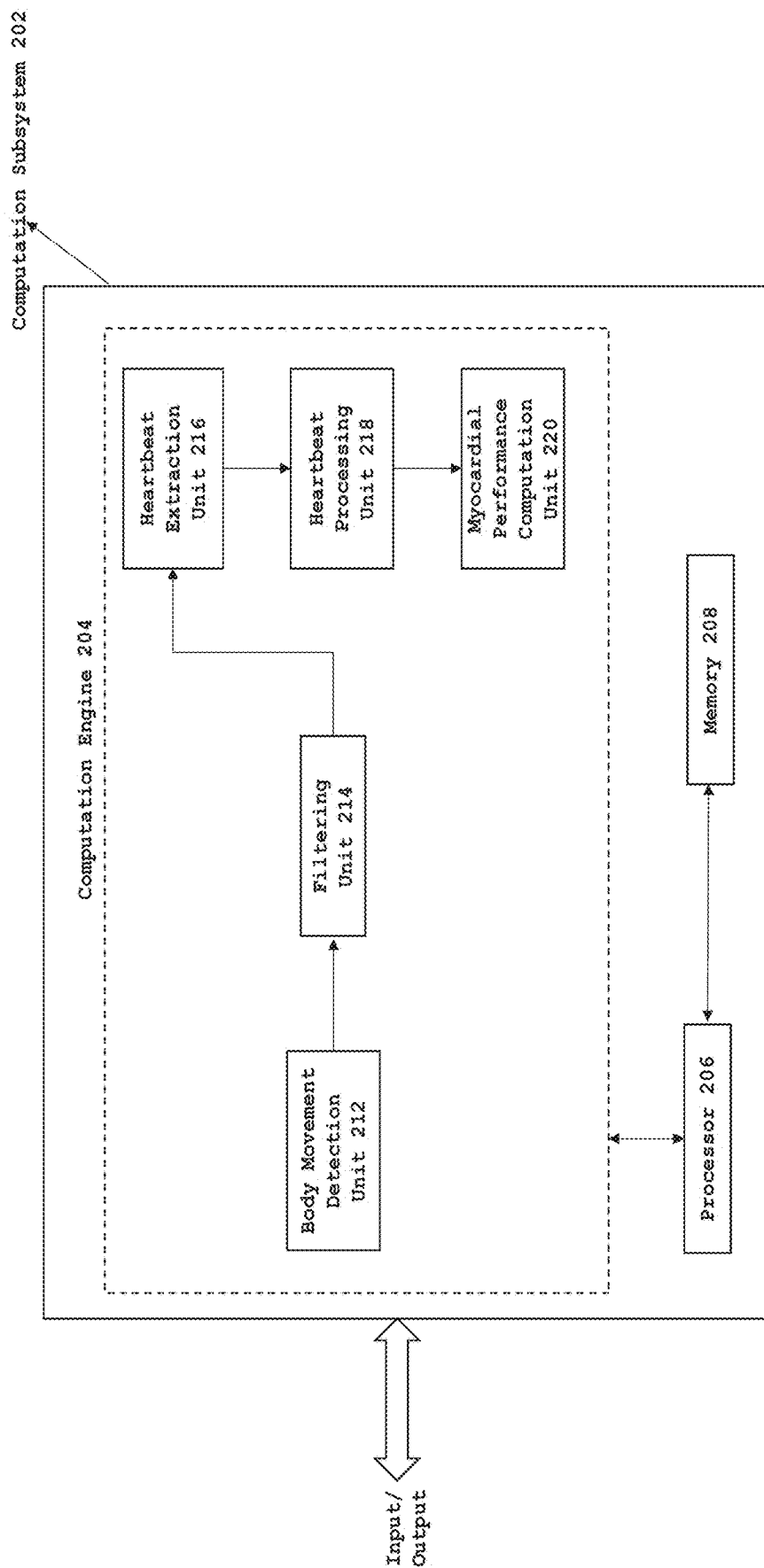
FIG. 2 illustrates a detailed block diagram of a computation subsystem, in accordance with an embodiment of the present invention.

FIG. 2 is a detailed block diagram of a computation subsystem 202, in accordance with various embodiments of the present invention. The computation subsystem 202 interfaces with database 118 (FIG. 1). The computation subsystem 202 is configured to invoke the database 118 (FIG. 1) for retrieving the stored micro-voltage digital datasets corresponding to cardiac cycles of the subject.

In an embodiment of the present invention, the computation subsystem 202 comprises a computation engine 204, a processor 206 and a memory 208. The computation engine 204 comprises various units which work in conjunction with each other. The various units of the engine 204 are operated via the processor 206 specifically programmed to execute instructions stored in the memory 208 for executing respective functionalities of the computation engine 204 in accordance with various embodiments of the present invention.

In an embodiment of the present invention, the computation subsystem 202 is configured to apply a pre-defined set of rules for processing micro-voltage digital datasets corresponding to the physiological parameters associated with the subject. The pre-defined set of rules are based on various empirical studies of physiological parameters data collected from prior experimentation, physiological parameters data collected from various subjects and data collected based on learning pattern developed over a period of time. In various embodiments of the present invention, the pre-defined set of rules may be updated from time-to-time by the subsystem 202. The computation engine 204 of the computation subsystem 202 is configured to apply the pre-defined set of rules for effective analysis, processing and identification of physiological parameters.

In an embodiment of the present invention, the computation engine 204 comprises a body movement detection unit 212, a filtering unit 214, a heartbeat extraction unit 216, a heartbeat processing unit 218 and a myocardial performance computation unit 220.

Figure 4:
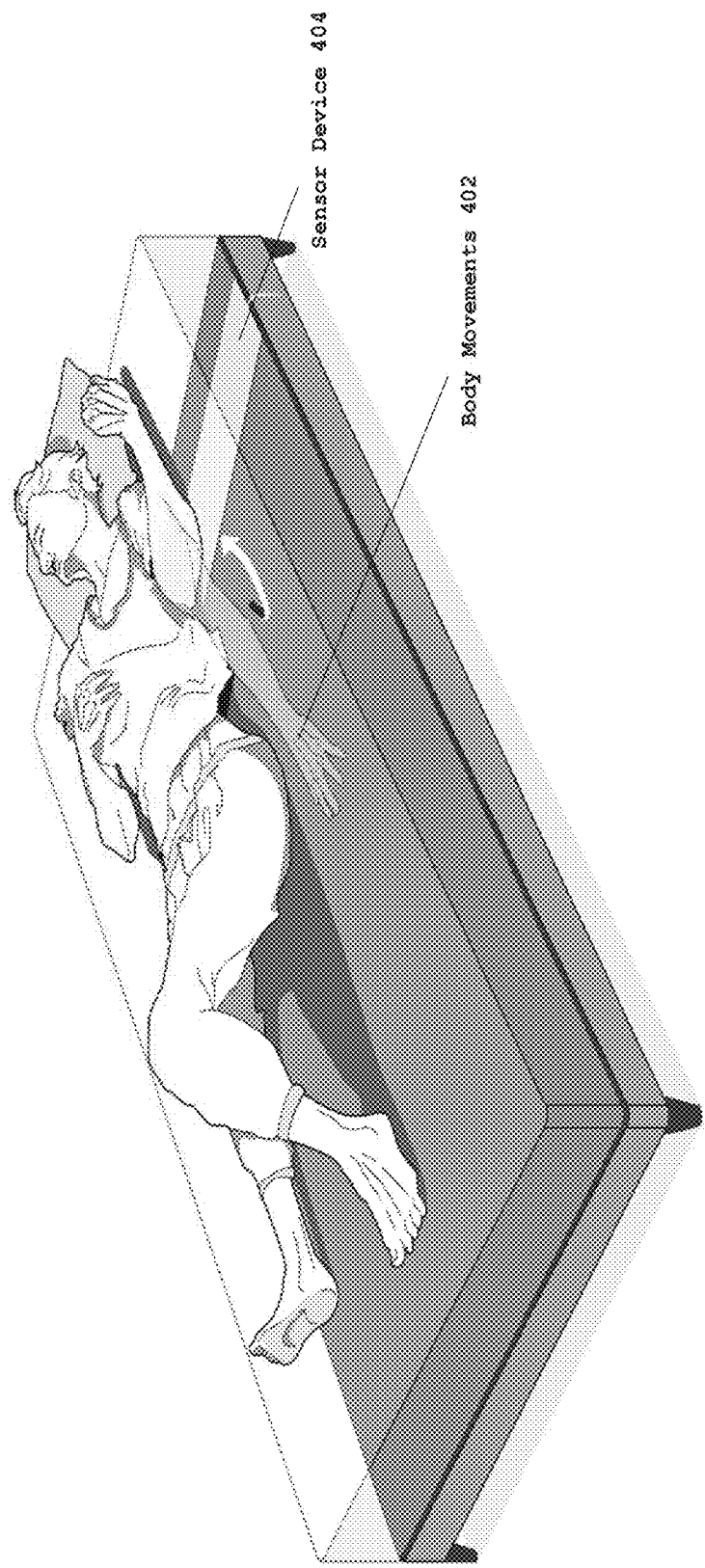
FIG. 4 illustrates a resting or a sleeping subject making certain body movements which are detected by the sensor device, in accordance with an embodiment of the present invention.

In operation, in an embodiment of the present invention, the body movement detection unit 212 of the computation engine 204 is configured to receive the stored micro-voltage digital datasets from the database 118 (FIG. 1). The body movement detection unit 212 is configured to analyze the micro-voltage digital datasets for extraction of 'body artifacts' element and 'body movement' element present in the micro-voltage digital datasets. The 'body artifacts' element and 'body movement' element are unwanted parts of the micro-voltage digital datasets. For instance, as illustrated in FIG. 4 when the subject is in a sleeping or resting state he/she may make certain body movements 402 which are detected by the sensor device 404 and extracted by the body movement detection unit 212 (FIG. 2). In an exemplary embodiment of the present invention, the body movement detection unit 212 is configured to compute the micro-voltage digital datasets as multiple dataset points, which are individual points, in an n-dimensional space. The body movement detection unit 212 is configured to subsequently apply unsupervised cognitive techniques such as, but are not limited to, density based spatial clustering of applications with noise (DBSCAN) technique etc. for clustering similar dataset points in the n-dimensional space to identify the 'body artifacts' elements and the 'body movements' element. In an exemplary embodiment of the present invention, the similar dataset points are clustered by the body movement detection unit 212 by calculating a Euclidean distance and further calculating a standard deviation between each point in the n-dimensional search space. In an exemplary embodiment of the present invention, the dataset points clustered are classified as 'body movements' element, and 'body artifacts' element. Example of the 'body movements' element may include, but are not limited to, unwanted body movements, and external movements. Example of the 'body artifacts' element may include, but are not limited to, twitches, external mechanical or electrical noise. The body movement detection unit 212 is configured to apply the pre-defined set of rules for removing and isolating the clusters relating to 'body movements' element and 'body artifacts' element from the micro-voltage digital datasets after clustering.

In an embodiment of the present invention, the filtering unit 214 of the computation engine 204 is configured to receive the micro-voltage digital datasets from the body movement detection unit 214 after removal of 'body movements' element and 'body artifacts' element. The filtering unit 214 is configured to further process the received micro-voltage digital datasets for computation of a 'biomarker'. The biomarker is representative of a cardiac cycle or a heart rate present in the micro-voltage digital datasets. Further, the filtering unit 214 may comprise digital filter, such as, but is not limited to, a bandpass butterworth filter etc. The bandpass butterworth filter is tuned at a bandpass frequency in the range of between 5 Hz to 15 Hz for efficient processing of the micro-voltage digital datasets and detection of the biomarker.

In an embodiment of the present invention, the computation engine 204 is configured to apply the pre-defined set of rules for efficiently transmitting the detected biomarker as multiple signal waveforms to the heartbeat extraction unit 216 from the filtering unit 214. The heartbeat extraction unit 216 is configured to process the received multiple signal waveforms associated with the biomarker for detecting a pre-defined parameter associated with the biomarker from a set of parameters. The pre-defined parameter associated with the biomarker is representative of time-domain heartbeat signal waveforms associated with the biomarker. The other parameters in the set of parameters may include snoring events, apnea-hypopnea events, breathing rate, irregular heartbeats (arrhythmias) etc. which may be extracted and stored in the database 118.

Figure 5:
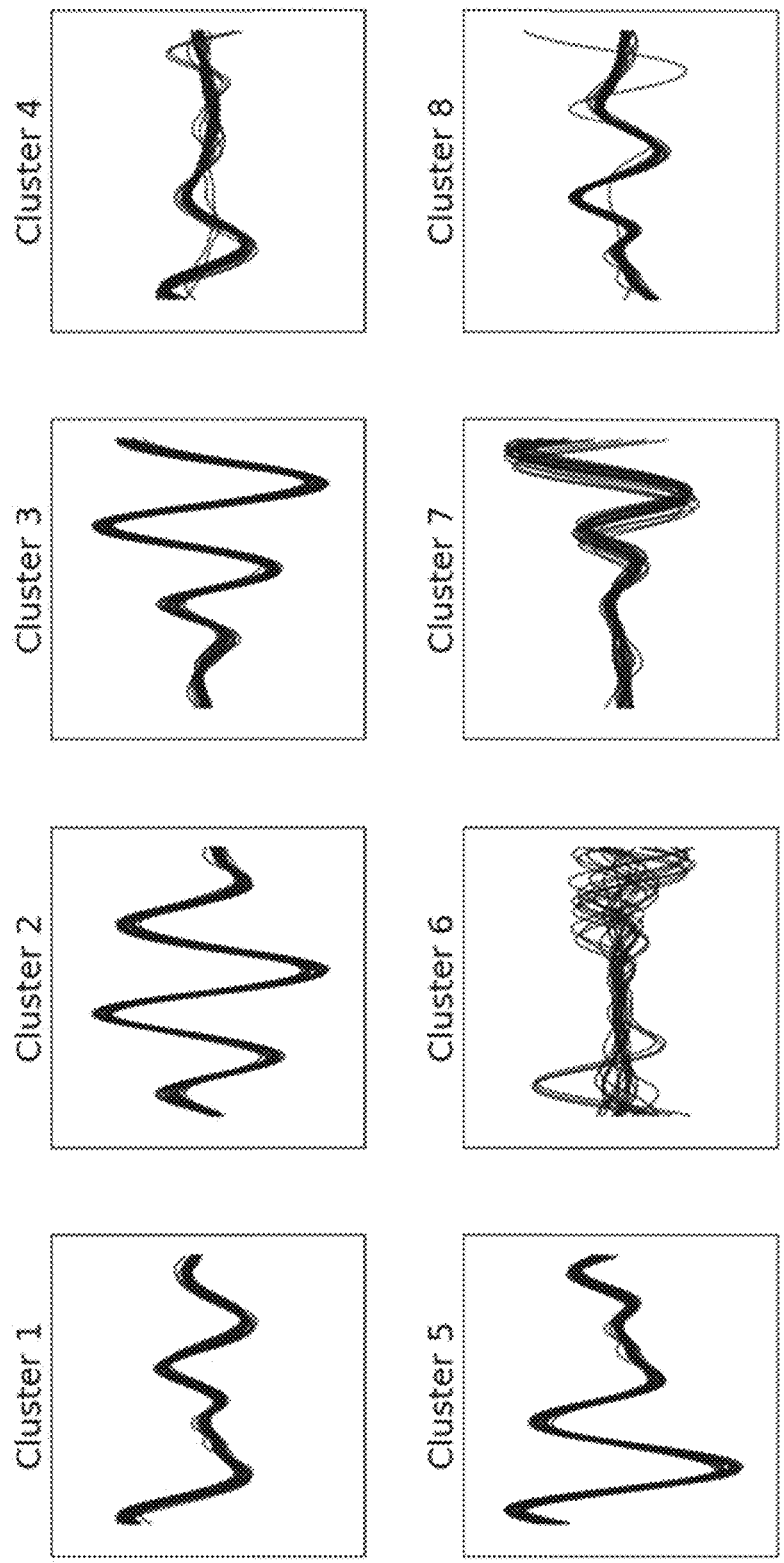
FIG. 5 illustrates eight clusters of clustered heartbeat signal templates, in accordance with an embodiment of the present invention

The heartbeat extraction unit 216 detects the pre-defined parameter associated with the biomarker by forming multiple templates corresponding to the parameter. In an exemplary embodiment of the present invention, the signal between three continuous maximas and two continuous minimas of the biomarker signal waveform are processed to form the heartbeat signal waveform template. The heartbeat extraction unit 216 subsequently assesses similarity between the heartbeat signal templates by applying unsupervised machine learning techniques such as, but is not limited to, clustering techniques for clustering the similar templates. In an exemplary embodiment of the present invention, the heartbeat extraction unit 216 is configured to cluster the formed templates, preferably, into eight clusters based on the Euclidean distance technique as illustrated in FIG. 5. Further, a principal template is selected by the heartbeat extraction unit 216 from the formed eight template clusters based on the frequency composition of the centroid template. The principal template is representative of a template cluster having maximum number of heartbeats. For instance, as illustrated in FIG. 5, cluster 2 has maximum number of heartbeats, and is therefore selected as the principal template. In an exemplary embodiment of the present invention, the principal template may further be selected based on a frequency analysis technique, a Fast Fourier Transform (FFT) technique etc. The principal template may comprise highest power in a desired frequency range relating to a heartbeat signal. Further, heartbeat signals are detected based on the formed principle templates. The detection of the heartbeat signals by the formation of principal template is referred to as phase 1 of heartbeat detection.

Figure 6:
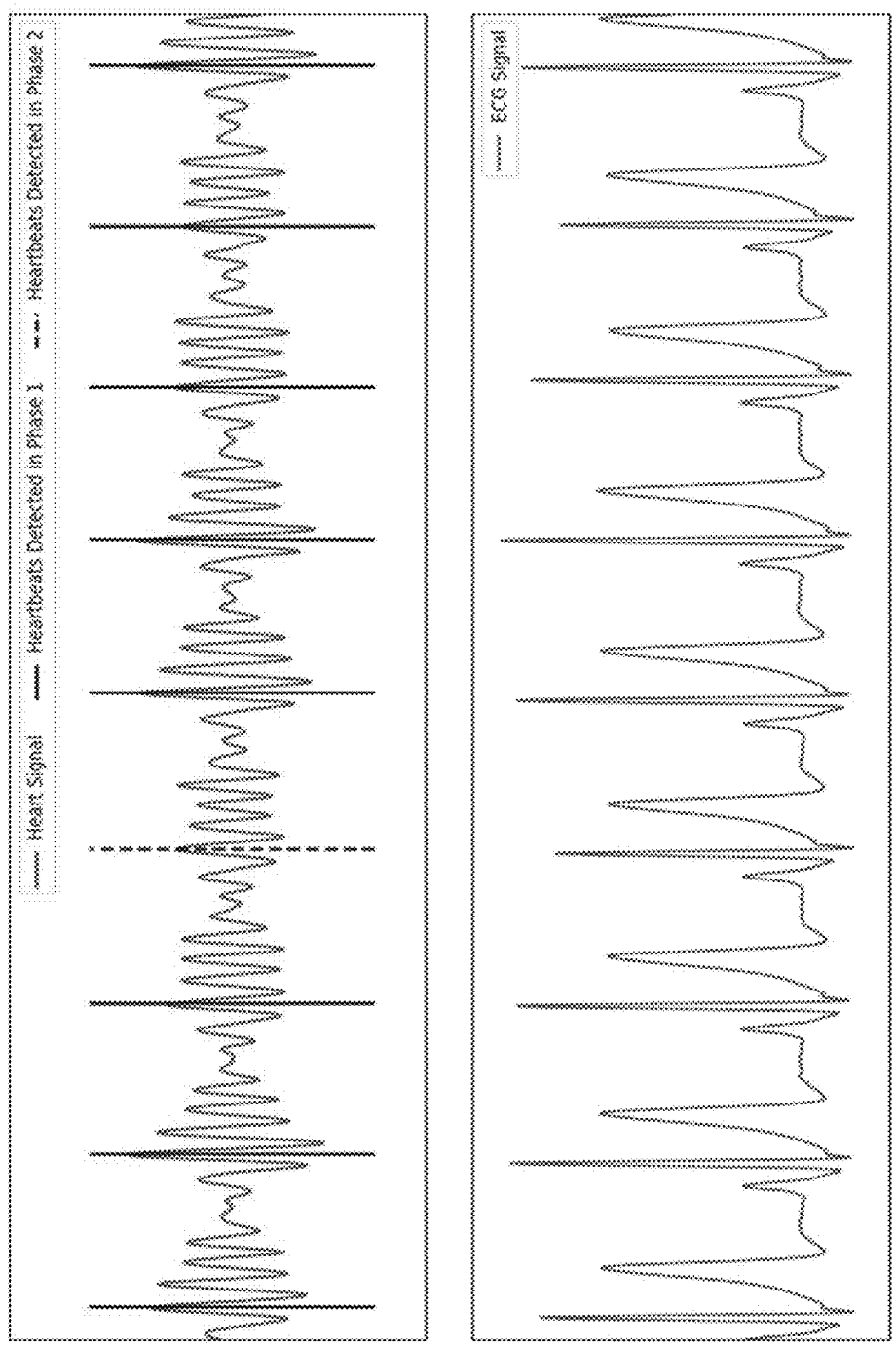
FIG. 6 illustrates a heartbeat signal detected, in accordance with an embodiment of the present invention, as compared to a conventional electrocardiogram (ECG)

In an embodiment of the present invention, one or more extracted heartbeat signals in the template form may be clustered by the heartbeat extraction unit 216 in a different cluster other than the clusters based on which the principal template is selected. The heartbeat extraction unit 216 is configured to analyze the detected heartbeat signals formed based on the principal template to identify potential instances of missing heartbeats by determining abnormal intervals between neighboring heartbeats. In an exemplary embodiment of the present invention, the identification of missing heartbeats is carried out based on correlation assessment techniques such as, but is not limited to, a Pearson correlation technique and is referred to as phase 2 of the heartbeat signals detection. Consequently, the missing heartbeats from the principal template are also detected and clustered appropriately. In an exemplary embodiment of the present invention, an abnormal interval in the clustering of the heartbeat templates is detected, if the time interval between two successive heartbeats is found to be considerably more than the average time interval between the successive heartbeats for a pre-defined period. The templates in that interval are then compared to a centroid of the selected cluster and the Pearson correlation coefficient is computed. Thereafter, if any template has a Pearson correlation coefficient, for example of at least of 0.8, it is selected as a heartbeat template. Further, individual heartbeats are detected based on the formed principle template. FIG. 6 illustrates heartbeat signals based on the principal template detected in the phase 1 and the missing heartbeat signals detected in the phase 2 compared to a conventional electrocardiogram signal (ECG) representing heart function. Advantageously, the heartbeat extraction unit 216, in accordance with various embodiments of the present invention, is capable of providing 96% accuracy in identification of heartbeats in comparison with conventional electrocardiogram (ECG) technique as illustrated in FIG. 6.

Figure 7:
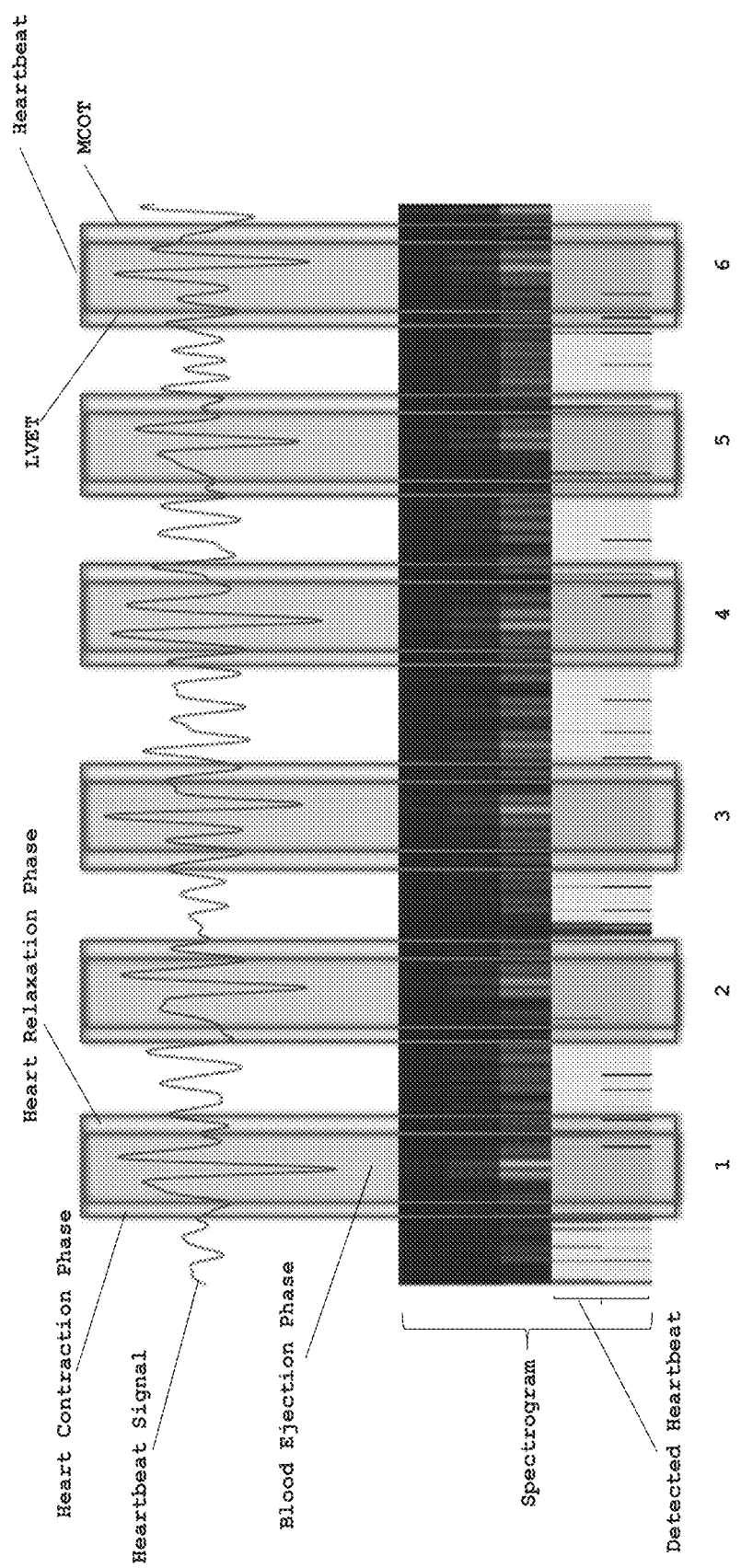
FIG. 7 illustrates a spectrogram based on the detected heartbeat along with multiple concentric rectangular boxes representing a heartbeat, in accordance with an embodiment of the present invention.

In another embodiment of the present invention, the heartbeat extraction unit 216 is configured to divide the detected heartbeat signals into short time intervals. The heartbeat signals are divided preferably into 5 second time intervals. In an exemplary embodiment of the present invention, the heartbeat extraction unit 216 is further configured to convert the divided heartbeat signals, which are time-domain signals, into frequency-domain signals i.e. to convert the time-domain parameter to frequency-domain parameter. In this exemplary embodiment of the present invention, the frequency-domain signals are obtained using Fourier Transform techniques such as, but are not limited to, a Short Term Fourier Transform (STFT) technique based on a pre-determined sampling rate. The frequency-domain signal of the heartbeat signals is obtained as an image representation in the form of a spectrogram. The pre-determined sampling rate may include, but is not limited to, 250 Hz, 500 Hz etc. The time-domain heartbeat signal is sampled as the frequency-domain at half the rate of the pre-determined sampling rate based on Nyquist sampling theorem technique. For example, if the sampling rate is 250 Hz for the time-domain heartbeat signal, then 125 Hz of it is sampled to frequency-domain. The spectrogram provides a visual representation (image) of the detected heartbeat signals, which are time-domain signals, as digital signals in frequency-domain along with the frequency power of each heartbeat signal in a particular frequency-domain. The frequency-domain may include, but is not limited to, 0-125 Hz, 0-250 Hz. Referring to FIG. 7, the spectrogram represents the heartbeat signal in the frequency-domain. In various embodiments of the present invention, the spectrogram represents each heartbeat signal in the form of specific color variations. For instance, if frequency-domain is in the range of 0-125 Hz, then the power of the signal is low in the high frequency range and high in the low frequency range. The low power towards the high frequency range is represented by a specific dark color in the spectrogram and high power towards the low frequency range is represented by a specific light color. The high power in the low frequency range (represented by light color) signifies occurrence of heartbeats and the low power in the high frequency range (represented by dark color) signifies absence of heartbeats. Therefore, the spectrogram is representative of location of heartbeats in the heartbeat signal present in the BCG signal.

Figure 8:
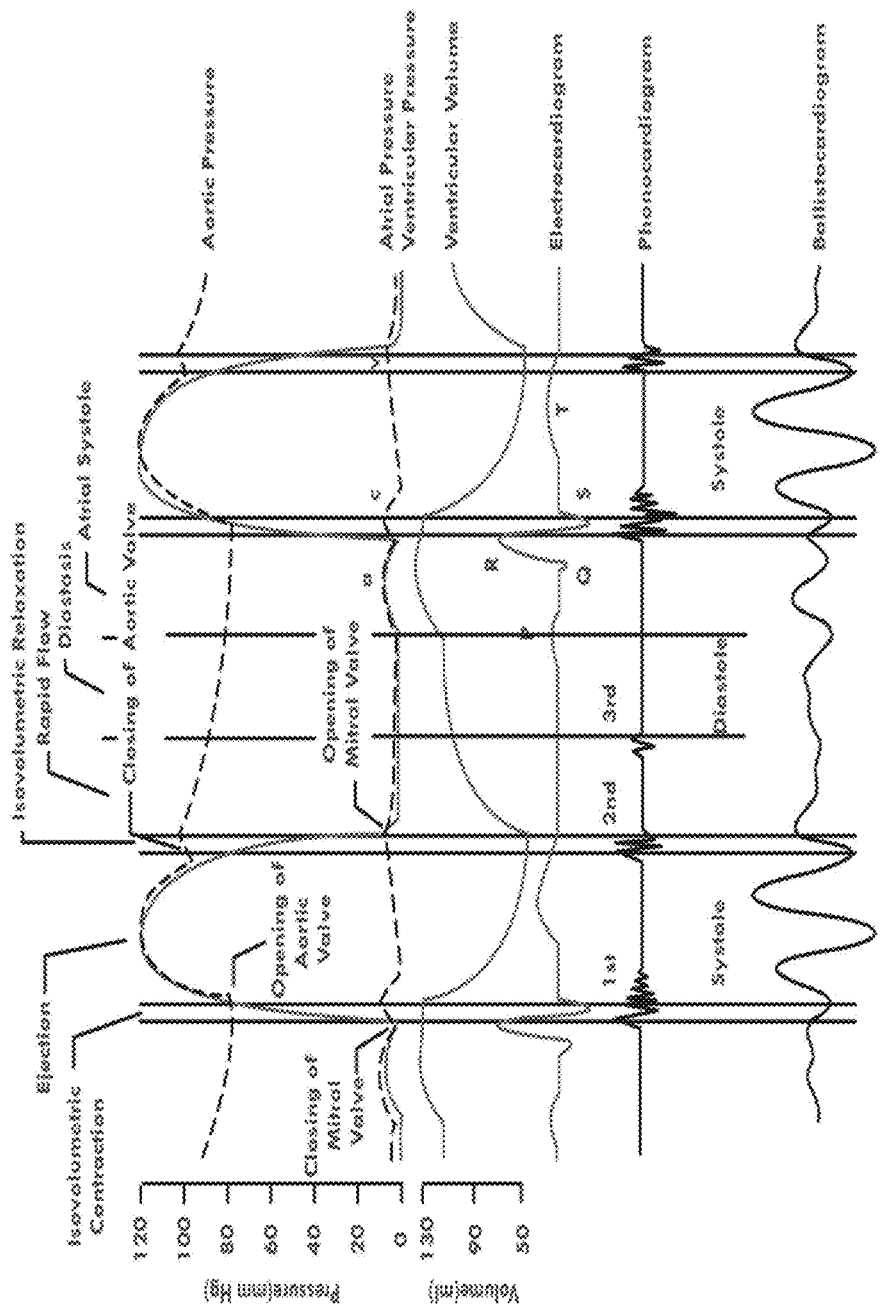
FIG. 8 illustrates a typical cardiac cycle in a graphical representation depicting opening and closing of heart valves along with systole and diastole phases.

In an embodiment of the present invention, the heartbeat processing unit 218 is configured to receive the spectrogram image representing the heartbeat signals in specific colors from the heartbeat extraction unit 216. The heartbeat processing unit 218 is configured to process the spectrogram image in order to determine a set of events representing specific patterns associated with cardiac cycle (biomarker) in each heartbeat signal present in the spectrogram image. The heartbeat processing unit 218 has an in-built intelligent mechanism for determining the set of events associated with each heartbeat signal in a cardiac cycle. A cardiac cycle, as illustrated in FIG. 8 in the form of a graphical representation, includes two phases i.e. diastole and systole and may further be illustrated in the form of an electrocardiogram, a phonocardiogram and a ballistocardiogram in FIG. 8. In the diastole phase blood returns to the heart from superior and interior vena cava and flows into right atrium. The pressure in the right atrium increases as blood flows into it. Further, when the pressure of the right atrium exceeds the pressure of right ventricle, tricuspid valve opens and passively allows blood to flow into the right ventricle. At the same instance, the oxygenated blood returning from the lungs flows into the left atrium. Further, as left atrial pressure increases, the mitral valve opens and blood flows into the left ventricle. In the systole phase, blood is forced to flow from the two atria into their respective ventricles as the atrial muscles contract due to the depolarization of the atria. Further, a period called isovolumetric contraction time (IVCT) during which the ventricles contract but the pulmonary and aortic valves are closed, as the ventricles do not have enough force to open them. The atrioventricular valves also remain closed during the isovolumetric contraction time period. Further, the semilunar valves open, when the ventricular muscle contracts and generates blood pressure within the ventricle higher than within the arterial tree. Further, when the heart muscle relaxes the diastole phase begins again.

In an embodiment of the present invention, the set of events is representative of features including heart contraction phase and heart relaxation phase based on opening and closing of aortic and mitral valves in each heartbeat, in accordance with an embodiment of the present invention. The heartbeat processing unit 218 is trained with multiple heartbeat signal snippets along with positions of opening and closing of aortic and mitral valves for each heartbeat. In an exemplary embodiment of the present invention, the heartbeat processing unit 218 employs cognitive techniques for processing the spectrogram image for computing specific patterns associated with each heartbeat in the cardiac cycle. The cognitive techniques may include, but are not limited to, machine learning techniques, deep learning techniques, such as, neural networks etc. The neural networks may include, but are not limited to, convolutional neural network (CNN), recurrent neural network (RNN) etc. Further, each heartbeat associated with a subject has specific patterns representing the set of events including cardiac cycles which may include, systole comprising heart contraction, blood ejection from heart and heart relaxation; diastole comprising heart relaxation and blood flowing into the heart; and opening and closing of heart valves.

In an embodiment of the present invention, the generated spectrogram representing the frequency-domain parameter in the heartbeat processing unit 218 is processed through a multi-level artificial neural network architecture for determining the set of events. The frequency-domain parameter is firstly processed at a first level of the neural network architecture to extract the features associated with the set of events. In an exemplary embodiment of the present invention, the first level comprises a time distributed convolutional 2D neural network level. The convolutional 2D neural network level processes the spectrogram image comprising the heartbeat signals and heartbeat locations to extract the features associated with the spectrogram image. Further, the extracted features represented in the spectrogram image are processed at a second level of the artificial neural network architecture. In an exemplary embodiment of the present invention, the second level comprises a time distributed Max Pooling 2D level for downsampling the extracted features. In an exemplary embodiment of the present invention, the heartbeat processing unit 218 is configured to repeat recursively the first step and the second step at the first level and the second level of neural network architecture respectively for a pre-defined number of times in order to effectively determine the set of events. For example, the pre-defined number of times may be at least three times (thrice). In various embodiments of the present invention, the set of events are generated in the form of a first dataset. In an example, the first dataset may include multi-dimensional data.

Further, in this embodiment, the heartbeat processing unit 218 is configured to process the first dataset at a third level of neural network architecture. In an exemplary embodiment of the present invention, the third level comprises a flattening level of a CNN. The flattening level is configured to convert the first dataset (multi-dimensional data) into a 1D tensor. Further, the heartbeat processing unit 218 is configured to process the 1D tensor at a fourth level of neural network architecture to generate a second dataset representing characteristics associated with the set of events. For instance, the characteristics may include patterns and time of occurrence of the set of events. In an exemplary embodiment of the present invention, the fourth level comprises a bi-directional Long Short Term Memory (Bi-LSTM) level. Advantageously, LSTM level effectively processes the short time heartbeat signals and analyzes the set of events for determining patterns and time of occurrence of the set of events. For example, the characteristics include determining the time of ejection of blood from heart, heart relaxation time, heart contraction time etc. Lastly, the heartbeat processing unit 218 is configured to process the second dataset at a fifth level of neural network architecture. In an exemplary embodiment of the present invention, the fifth level comprises a time distributed dense level for computing a set of values corresponding to the set of events. The set of values are computed in time-domain from the set of events which are in the frequency-domain. In an exemplary embodiment of the present invention, the set of values represent time-based features of the heartbeat signal (parameter) such as, isovolumetric contraction time (IVCT) in a range of between 20 ms and 70 ms, isovolumetric relaxation time (IVRT) in a range of between 50 ms and 90 ms, left ventricular ejection time (LVET) in a range of between 150 ms and 350 ms and mitral closing to opening time (MCOT). In another exemplary embodiment of the present invention, the set of values are computed by consecutively inserting multiple two concentric rectangular bounding boxes around the heartbeat signal (pre-determined parameter) provided in the spectrogram image, as illustrated in FIG. 7, based on the learning and training carried out previously. Further, each of the rectangular boxes as illustrated in FIG. 7 represents a heartbeat, outer box represents MCOT and inner box represents LVET. Further, six heartbeats are represented in FIG. 7. It must be understood that FIG. 7 is only illustrative and the number of boxes is not limited to six and may be more than six with respect to various embodiments of the present invention. Further, as represented in concentric rectangular boxes '1', the left hand side gap between the concentric boxes represents heart contraction phase and right hand side gap between the concentric boxes represents heart relaxation phase and the middle portion of the concentric boxes represents the blood ejection phase which is representative of the closing and opening of the heart valves respectively, which relates to the set of values. Advantageously, the set of values computed by the heartbeat processing unit 218 are 95% accurate with respect to the measurements carried out utilizing a conventional echocardiography machine.

In an embodiment of the present invention, the myocardial performance computation unit 220 is configured to receive the computed set of values from the heartbeat processing unit 218. The myocardial performance computation unit 220 is further configured to analyze the computed set of values for determining the myocardial performance by computing a myocardial performance index (MPI). MPI is associated with time intervals between consecutive heartbeats of the subject and represents ratio of the total non-ejection time-period to total ejection time-period which determines the myocardial performance of the heart. Higher MPI is an indication of a lower ejection ratio and vice-versa. MPI, therefore, is an effective indicator of heart failure and aids to determine left ventricular (LV) dysfunction. An MPI value above 0.45 indicates abnormal functioning of LV (mild and moderate LV dysfunction) and above 0.7 indicates severe LV dysfunction.

In an exemplary embodiment of the present invention, the myocardial performance index (MPI) value is computed by the myocardial performance computation unit 220 based on a myocardial performance index (MPI) formula represented below using the computed set of values:

$$LVMPI = \frac{IVCT + IVRT}{LVET} = \frac{MCOT - LVET}{LVET}$$

In various embodiments of the present invention, as aforementioned, the set of values include IVCT, IVRT, LVET and MCOT values. In an embodiment of the present invention, set of events, and set of values associated with the calculated MPI biomarker to the database for storage and future retrieval.

In an embodiment of the present invention, the computation subsystem 202 is configured to transmit the computed biomarker, the set of events and the set of values associated with the computed MPI to the database 118 (FIG. 1) for storage and future retrieval.

In an embodiment of the present invention, the data visualization unit 128 is configured to communicate with the database 118 in order to retrieve the stored set of events, set of values and MPI values for viewing by the subject via the data visualization unit 128. The data visualization unit 128 is configured to uniquely authorize each subject by registering and providing authorization to subjects for viewing the stored set of events, set of values and MPI values associated with a particular subject. The data visualization unit 128 may be accessed by a doctor or a subject's caretaker for viewing the heart rate related data of the subject based on the authorization provided by the subject to the doctor or the caretaker. Further, the data visualization unit 128 may be via an application, a dashboard based web application etc. providing a graphical user interface (GUI) to the subject for accessing the database 118 for viewing the set of events, set of values and MPI values stored in the database 118. The data visualization unit 128 may be configured on, but is not limited to, a smart phone, a tablet, a computer system, a smart watch etc. The data visualization unit 128 is therefore configured to provide the set of events, set of values, calculated MPI values, tachogram related to heartbeats, heart rate of the subject etc. to the subject, subject's caretaker, doctor, etc.

Advantageously, in accordance with various embodiments of the present invention, the system 100 is configured to efficiently monitor cardiac activity of a subject in real-time for myocardial performance detection without any human intervention. The system 100 is configured to efficiently detect BCG signals related to the subject in a contactless manner and automatically compute MPI. The system 100 is configured with in-built intelligent mechanism for determination of opening and closing of heart valves during each heartbeat based on the detected heartbeats in BCG signals and subsequently calculate time-period of the valves opening and closing for MPI calculation. Further, any irregularity in the time-period of valves opening and closing aids in determining any anomalies related to the heart which may be an indication of cardiovascular diseases is detected by the system 100. The system 100 is configured to regularly and continuously measure cardiac activity of the subject in an unobtrusive manner with precision and accuracy and eliminates the need of spot checkups by the physician for cardiac activity monitoring. Further, the system 100 may be applied for monitoring a patient having heart related diseases or a healthy person in order to prevent any future occurrence of cardiovascular diseases, such as, heart attack, stroke, heart muscle dysfunction etc. Further, the system 100 is easily deployable, easily implementable, does not cause any inconvenience to the subject, portable and cost effective.

Figure 9:
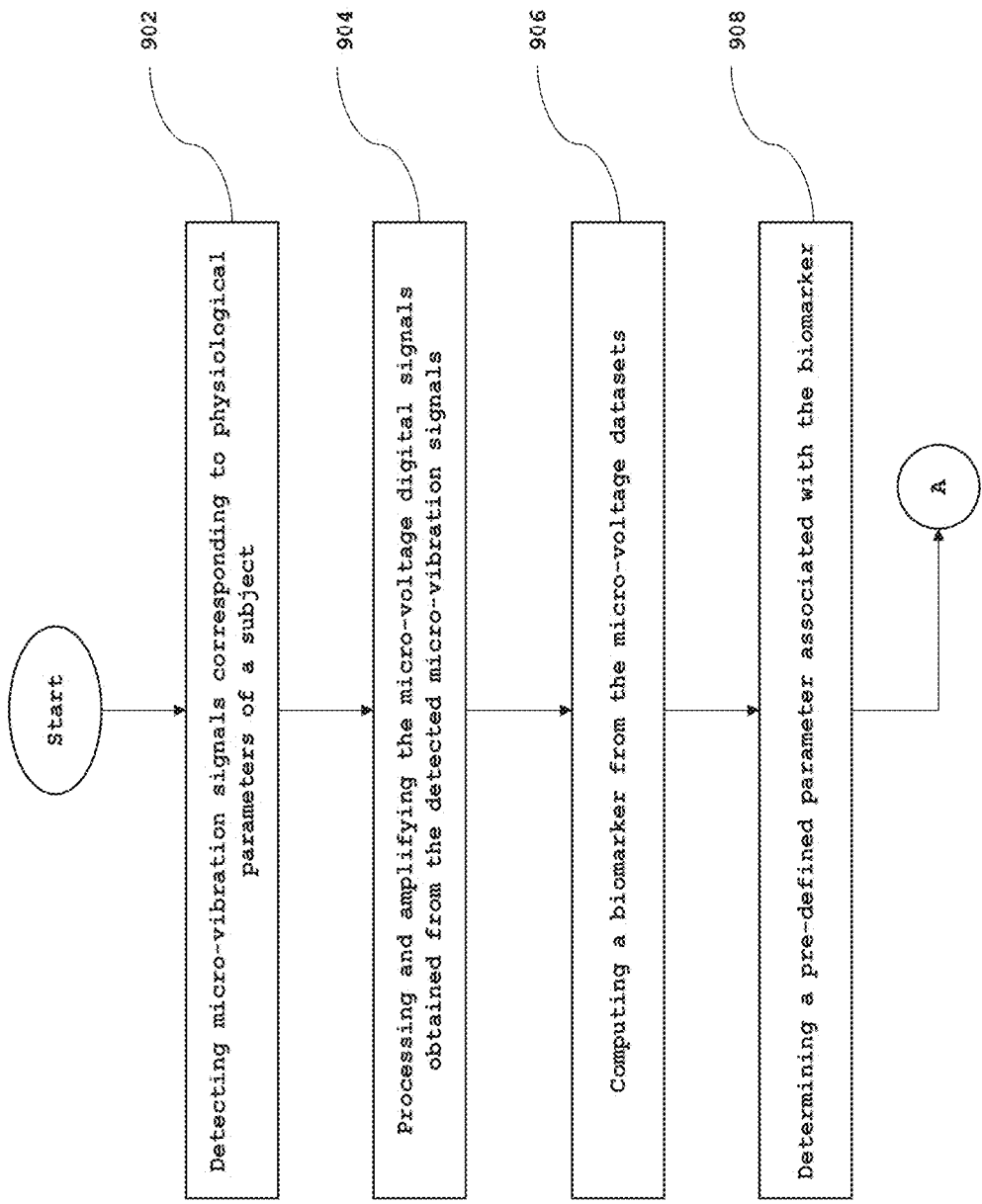

FIG. 9 and FIG. 9A is a flowchart illustrating a method for contactless monitoring of cardiac activity for myocardial performance determination, in accordance with various embodiments of the present invention.

At step 902, micro-vibration signals corresponding to physiological parameters of a subject are detected. In an embodiment of the present invention, the micro-vibrations corresponding to physiological parameters of the subject are detected and captured as analog data signals in a contactless manner. The micro-vibrations are captured and received through a medium placed between the subject and a sensor device. For example, the micro-vibrations may be captured through a medium ranging from a thin surface to a thick surface such as a 20-inch mattress. The micro-vibrations captured may include, but are not limited to, ballistocardiographic (BCG) signals associated with physiological parameters of the subject such as heart rates, heart movements, chest movements, body movements, respiration signals etc. Further, the captured micro-vibrations, which are analog signals, are converted into micro-voltage digital signals. The micro-voltage digital signals may be in the range of between 0 V-3.3 V.

At step 904, the micro-voltage digital signals obtained from the detected micro-vibration signals are processed and amplified. In an embodiment of the present invention, the micro-voltage digital signals and record the received micro-voltage digital signal in a pre-defined data recording format. The pre-defined data recording format may include, but is not limited to, a chronological order format. In an embodiment of the present invention, the micro-voltage digital signals are amplified for maximizing resolution of the micro-voltage digital signals, as desired, to accurately process the micro-voltage digital signals for efficient detection of subject's physiological parameters. The maximization of resolution of micro-voltages digital signal is carried out without data loss or information loss that may occur due to clipping. Multiple amplification capabilities for amplifying the micro-voltage digital signal are provided depending upon the strength of the micro-voltage digital signals. In an exemplary embodiment of the present invention, the multiple amplification capabilities provides, but are not limited to, eight different amplification options that amplify the micro-voltages between the range of 15× to 2500×. Automatic calibration and selection of the amplification option is provided. A sensitivity shifting mechanism is utilized for automatically calibrating and selecting the amplification option. The sensitivity shifting mechanism depends upon the level of strength of the micro-voltage digital signals.

In an embodiment of the present invention, the amplified micro-voltage digital signal is transmitted to a database via a communication channel (not shown). The communication channel (not shown) may include, but is not limited to, a wire or a logical connection over a multiplexed medium, such as, a radio channel in telecommunications and computer networking. Examples of telecommunications and computer networking may include a local area network (LAN), a metropolitan area network (MAN), a wide area network (WAN) or any wired or wireless network, such as, but is not limited to, Wi-Fi, Bluetooth Classic, Bluetooth Low Energy etc. In an exemplary embodiment of the present invention, the database may be installed on a smartphone, tablet, laptop, computer system etc. of the subject. In another exemplary embodiment of the present invention, the database may be positioned in a cloud based server. In an embodiment of the present invention, the database is configured to store the micro-voltage digital signal in a pre-defined data storage format which may include, but is not limited to, one or more datasets in a chronological order format in the form of micro-voltage digital datasets.

At step 906, a biomarker is extracted from the micro-voltage datasets. In an embodiment of the present invention, a pre-defined set of rules are applied for processing the micro-voltage datasets corresponding to the physiological parameters associated with the subject. The set of pre-defined rules are based on various empirical studies of physiological parameter data collected from prior experimentation, physiological parameter data collected from various subjects and data collected based on learning pattern developed over a period of time. In various embodiments of the present invention, the set of pre-defined rules may be updated from time-to-time. The set of rules are applied for effective analysis, processing and identification of physiological parameter.

In operation, in an embodiment of the present invention, the micro-voltage digital datasets are analyzed for extraction of 'body artifacts' element and 'body movement' element present in the micro-voltage digital datasets. The 'body artifacts' element and 'body movement' element are unwanted parts of the micro-voltage digital datasets. In an exemplary embodiment of the present invention, the micro-voltage digital datasets are computed as multiple dataset points, which are individual points, in an n-dimensional space. Subsequently, unsupervised cognitive techniques are applied such as, but are not limited to, density based spatial clustering of applications with noise (DBSCAN) technique etc. for clustering similar dataset points in the n-dimensional space to identify the 'body artifacts' elements and the 'body movements' element. In an exemplary embodiment of the present invention, the similar dataset points are clustered by calculating a Euclidean distance and further calculating a standard deviation between each point in the n-dimensional search space. In an exemplary embodiment of the present invention, the dataset points clustered are classified as 'body movements' element, and 'body artifacts' element. Example of the 'body movements' element may include, but are not limited to, unwanted body movements, and external movements. Example of the 'body artifacts' element may include, but are not limited to, twitches, external mechanical or electrical noise. The pre-defined set of rules are applied for removing and isolating the clusters relating to 'body movements' element and 'body artifacts' element from the micro-voltage digital datasets after clustering.

In an embodiment of the present invention, the received micro-voltage digital datasets are processed utilizing a digital filtering technique for computation of a 'biomarker'. The filtering technique utilized may include, but is not limited to, a bandpass butterworth filtering technique, which is tuned at a bandpass frequency in the range of between 5 Hz and 15 Hz for efficient processing of the micro-voltage digital datasets and extraction of the biomarker. The biomarker is representative of a cardiac cycle or heart rate present in the micro-voltage digital datasets.

At step 908, a pre-defined parameter associated with the biomarker is determined. In an embodiment of the present invention, the multiple signal waveforms associated with the biomarker are processed for detecting a pre-defined parameter associated with the biomarker from a set of parameters. The pre-defined parameter associated with the biomarker is representative of time-domain heartbeat signal waveforms associated with the biomarker. The time-domain pre-defined parameter is detected by forming multiple templates corresponding to the parameter. In an exemplary embodiment of the present invention, the signal between three continuous maximas and two continuous minimas of the biomarker signal waveform are processed to form the heartbeat signal waveform template. Subsequently, similarity between the heartbeat signal templates is assessed by applying unsupervised machine learning techniques such as, but is not limited to, clustering techniques for clustering the similar templates. In an exemplary embodiment of the present invention, the formed templates are clustered, preferably, into eight clusters based on the Euclidean distance technique. Further, a principal template is selected from the formed eight template clusters based on the frequency composition of the centroid template. The principal template is representative of a template cluster having maximum number of heartbeats. In an exemplary embodiment of the present invention, the principal template may further be selected based on a frequency analysis technique, a Fast Fourier Transform (FFT) technique etc. The principal template may comprise highest power in a desired frequency range relating to a heartbeat signal. Further, heartbeat signals are detected based on the formed principle templates. The detection of the heartbeat signals by the formation of principal template is referred to as phase 1 of heartbeat detection.

In an embodiment of the present invention, one or more extracted heartbeat signals in the template form may be clustered in a different cluster other than the clusters based on which the principal template is selected. The detected heartbeat signals formed based on the principal template are analyzed to identify potential instances of missing heartbeats by determining abnormal intervals between neighboring heartbeats. In an exemplary embodiment of the present invention, the identification of missing heartbeats is carried out based on correlation assessment techniques such as, but is not limited to, a Pearson correlation technique and is referred to as phase 2 of the heartbeat signals detection. Consequently, the missing heartbeats from the principal template are also detected and clustered appropriately. In an exemplary embodiment of the present invention, an abnormal interval in the clustering of the heartbeat templates is detected, if the time interval between two successive heartbeats is found to be considerably more than the average time interval between the successive heartbeats for a pre-determined period. The templates in that interval are then compared to a centroid of the selected cluster and the Pearson correlation coefficient is computed. Thereafter, if any template has Pearson correlation coefficient, for example of at least of 0.8, it is selected as a heartbeat template. Further, individual heartbeats are detected based on the formed principle template.

At step 910, the time-domain pre-defined parameter is converted to a frequency-domain parameter. In an embodiment of the present invention, the pre-defined parameter is divided into multiple time intervals and subsequently the divided parameter is converted into an image representation. In an exemplary embodiment of the present invention, the detected time-domain heartbeat signals are divided into short time intervals. The heartbeat signals are divided preferably into 5 second time intervals. The divided heartbeat signals, are then converted into frequency-domain signals to obtain the frequency-domain parameter. In this exemplary embodiment of the present invention, the frequency-domain signals are obtained using Fourier Transform techniques such as, but are not limited to, a Short Term Fourier Transform (STFT) technique based on a pre-determined sampling rate. The frequency-domain signal of the heartbeat signals is obtained as an image representation in the form of a spectrogram. The pre-determined sampling rate may include, but is not limited to, 250 Hz, 500 Hz etc. The time-domain heartbeat signal is sampled as the frequency-domain at half the rate of the pre-determined sampling rate based on Nyquist sampling theorem technique. For example, if the sampling rate is 250 Hz for the time-domain heartbeat signal, then 125 Hz of it is sampled to frequency-domain. The spectrogram provides a visual representation (image) of the detected heartbeat signals, which are time-domain signals, as digital signals in frequency-domain along with the frequency power of each heartbeat signal in a particular frequency-domain. The frequency-domain may include, but is not limited to, 0-125 Hz, 0-250 Hz. In various embodiments of the present invention, the spectrogram represents each heartbeat signal in the form of specific color variations. For instance, if frequency-domain is in the range of 0-125 Hz, then the power of the signal is low in the high frequency range and high in the low frequency range. The low power towards the high frequency range is represented by a specific dark color in the spectrogram and high power towards the low frequency range is represented by a specific light color. The high power in the low frequency range (represented by light color) signifies occurrence of heartbeats and the low power in the high frequency range (represented by dark color) signifies absence of heartbeats. Therefore, the spectrogram is representative of location of the heartbeats in heartbeat signal present in the BCG signal.

At step 912, a set of events is determined. In an embodiment of the present invention, spectrogram image comprising the heartbeat signal represented in specific color and heartbeat locations in the frequency-domain is processed to compute a set of events representing specific patterns associated with cardiac cycle (biomarker) in each heartbeat signal present in the spectrogram image. The set of events is representative of features including heart contraction phase and heart relaxation phase based on opening and closing of aortic and mitral valves in each heartbeat, in accordance with an embodiment of the present invention. In an exemplary embodiment of the present invention, various cognitive techniques are employed for processing the spectrogram image for computing specific patterns associated with each heartbeat in the cardiac cycle. The cognitive techniques may include, but are not limited to, machine learning techniques, deep learning techniques such as, artificial neural networks etc. The neural networks may include, but are not limited to, convolutional neural network (CNN), recurrent neural network (RNN) etc. Further, each heartbeat associated with a subject has specific patterns representing the set of events including cardiac cycles which may include, systole comprising heart contraction, blood ejection from heart and heart relaxation; diastole comprising heart relaxation and blood flowing into the heart; and opening and closing of heart valves.

In an embodiment of the present invention, the generated spectrogram is processed through a multi-level artificial neural network architecture for determining the set of events. The frequency-domain parameter represented in the spectrogram image is firstly processed at a first level of the neural network architecture to extract the features associated with the set of events. In an exemplary embodiment of the present invention, the first level comprises a time distributed convolutional 2D neural network level. The convolutional 2D neural network level processes the spectrogram image comprising the heartbeat signals and heartbeat locations to extract the features associated with the spectrogram image. Further, the extracted features represented in the spectrogram image are processed at a second level of artificial neural architecture. In an exemplary embodiment of the present invention, the second level comprises a time distributed Max Pooling 2D level for downsampling the extracted features. In an exemplary embodiment of the present invention, processing of the extracted features representing the set of events at the first level and the second level of neural network architecture are recursively repeated for a pre-defined number of times in order to effectively determine the set of events. For example, the pre-defined number of times may be at least three times (thrice). In various embodiments of the present invention, the generated set of events are in the form of a first dataset. In an example, the first dataset may include multi-dimensional data.

Further, in this embodiment, the first dataset is processed at a third level of neural network architecture. In an exemplary embodiment of the present invention, the third level comprises a flattening level of a CNN. The flattening level is configured to convert the first dataset (multi-dimensional) data into a 1D tensor. Further, the 1D tensor is processed at a fourth level of neural network architecture to generate a second dataset representing characteristics associated with the set of events. For instance, the characteristics may include patterns and time of occurrence of the set of events. In an exemplary embodiment of the present invention, the fourth level comprises a bi-directional Long Short Term Memory (Bi-LSTM) level. For example, the characteristics include determining the time of ejection of blood from heart, heart relaxation time, heart contraction time etc.

At step 914, a set of values is computed based on the set of events. In an embodiment of the present invention, lastly, the second dataset is processed at a fifth level of neural network architecture. In an exemplary embodiment of the present invention, the fifth level, comprises a time distributed dense level for computing the set of values corresponding to the set of events. The set of values are computed in time-domain from the set of events which are in the frequency-domain. In an exemplary embodiment of the present invention, the set of values represents time-based features of the heartbeat signal (parameter) such as, isovolumetric contraction time (IVCT) in a range of between 20 ms and 70 ms, isovolumetric relaxation time (IVRT) in a range of between 50 ms and 90 ms, left ventricular ejection time (LVET) in a range of between 150 ms and 350 ms and mitral closing to opening time (MCOT). In another exemplary embodiment of the present invention, the set of values are computed by consecutively inserting multiple two concentric rectangular bounding boxes around the heartbeat signal (pre-determined parameter) provided in the spectrogram image, based on the learning and training carried out previously. Further, each of the rectangular boxes as represents a heartbeat, outer box represents MCOT and inner box represents LVET. Further, with respect to concentric rectangular boxes, the left hand side gap between the concentric boxes represents heart contraction phase and right hand side gap between the concentric boxes represents heart relaxation phase and the middle portion of the concentric boxes represents the blood ejection phase which is representative of the closing and opening of the heart valves respectively, which relates to the set of values.

At step 916, myocardial performance index is computed based on the set of values. In an embodiment of the present invention, the computed set of values are analyzed for determining the myocardial performance by computing the myocardial performance index (MPI). MPI is associated with time intervals between consecutive heartbeats of the subject and represents ratio of the total non-ejection time period to total ejection time-period which determines the myocardial performance of the heart. Higher MPI is an indication of a lower ejection ratio and vice versa. MPI, therefore, is an effective indicator of heart failure and aids to determine left ventricular (LV) dysfunction. An MPI value above 0.45 indicates abnormal functioning of LV (mild and moderate LV dysfunction) and above 0.7 indicates severe LV dysfunction.

In an exemplary embodiment of the present invention, the myocardial performance index (MPI) value is computed based on a myocardial performance index (MPI) formula represented below using the computed set of values:

$$LVMPI = \frac{IVCT + IVRT}{LVET} = \frac{MCOT - LVET}{LVET}$$

In various embodiments of the present invention, as aforementioned, the set of values include IVCT, IVRT, LVET and MCOT values. In an embodiment of the present invention, set of events and set of values associated with the calculated MPI to the database for storage and future retrieval.

In an embodiment of the present invention, the stored set of events, set of values and MPI values are retrieved by the subject for viewing. Each subject is uniquely authorized by registering and providing authorization to subjects for viewing the stored set of events, set of values and MPI values associated with a particular subject. A doctor or a subject's caretaker may also be able to view the heart rate related data of the subject based on the authorization provided by the subject to the doctor or the caretaker. The data may be viewed via an application, a dashboard based web application etc. providing a graphical user interface (GUI) to the subject for accessing the database for viewing the set of events, set of values and MPI values stored in the database.

Therefore, the set of events, set of values, calculated MPI values, tachogram related to heartbeats, heart rate of the subject etc. are provided to the subject, subject's caretaker, doctor, etc.

FIG. 10 illustrates an exemplary computer system in which various embodiments of the present invention may be implemented. The computer system 1002 comprises a processor 1004 and a memory 1006. The processor 1004 executes program instructions and is a real processor. The computer system 1002 is not intended to suggest any limitation as to scope of use or functionality of described embodiments. For example, the computer system 1002 may include, but not limited to, a programmed microprocessor, a micro-controller, a peripheral integrated circuit element, and other devices or arrangements of devices that are capable of implementing the steps that constitute the method of the present invention. In an embodiment of the present invention, the memory 1006 may store software for implementing various embodiments of the present invention. The computer system 1002 may have additional components. For example, the computer system 1002 includes one or more communication channels 1008, one or more input devices 1010, one or more output devices 1012, and storage 1014. An interconnection mechanism (not shown) such as a bus, controller, or network, interconnects the components of the computer system 1002. In various embodiments of the present invention, operating system software (not shown) provides an operating environment for various softwares executing in the computer system 1002, and manages different functionalities of the components of the computer system 1002.

The communication channel(s) 1008 allow communication over a communication medium to various other computing entities. The communication medium provides information such as program instructions, or other data in a communication media. The communication media includes, but not limited to, wired or wireless methodologies implemented with an electrical, optical, RF, infrared, acoustic, microwave, Bluetooth or other transmission media.

The input device(s) 1010 may include, but not limited to, a keyboard, mouse, pen, joystick, trackball, a voice device, a scanning device, touch screen or any another device that is capable of providing input to the computer system 1002. In an embodiment of the present invention, the input device(s) 1010 may be a sound card or similar device that accepts audio input in analog or digital form. The output device(s) 1012 may include, but not limited to, a user interface on CRT or LCD, printer, speaker, CD/DVD writer, or any other device that provides output from the computer system 1002.

The storage 1014 may include, but not limited to, magnetic disks, magnetic tapes, CD-ROMs, CD-RWs, DVDs, flash drives or any other medium which can be used to store information and can be accessed by the computer system 1002. In various embodiments of the present invention, the storage 1014 contains program instructions for implementing the described embodiments.

The present invention may suitably be embodied as a computer program product for use with the computer system 1002. The method described herein is typically implemented as a computer program product, comprising a set of program instructions which is executed by the computer system 1002 or any other similar device. The set of program instructions may be a series of computer readable codes stored on a tangible medium, such as a computer readable storage medium (storage 1014), for example, diskette, CD-ROM, ROM, flash drives or hard disk, or transmittable to the computer system 1002, via a modem or other interface device, over either a tangible medium, including but not limited to optical or analogue communications channel(s) 1008. The implementation of the invention as a computer program product may be in an intangible form using wireless techniques, including but not limited to microwave, infrared, Bluetooth or other transmission techniques. These instructions can be preloaded into a system or recorded on a storage medium such as a CD-ROM, or made available for downloading over a network such as the internet or a mobile telephone network. The series of computer readable instructions may embody all or part of the functionality previously described herein.

The present invention may be implemented in numerous ways including as a system, a method, or a computer program product such as a computer readable storage medium or a computer network wherein programming instructions are communicated from a remote location.

While the exemplary embodiments of the present invention are described and illustrated herein, it will be appreciated that they are merely illustrative. It will be understood by those skilled in the art that various modifications in form and detail may be made therein without departing from or offending the spirit and scope of the invention.

We claim:

1. A system for myocardial performance determination, the system comprising:
a memory storing program instructions;
a processor configured to execute the instructions stored in the memory; and
a computation engine executed by the processor and configured to:
generate a first dataset representing a set of events associated with a pre-defined parameter of a biomarker extracted from physiological parameters of a subject, wherein the physiological parameters are associated with ballistocardiographic (BCG) signals that are received from a sensor device that captures micro-vibrations from the subject in a contact-less manner, and wherein the set of events is determined by processing the pre-defined parameter at a first level and a second level of a multi-level artificial neural network architecture recursively for a pre-defined number of times to generate a multi-dimensional data, the set of events represent patterns associated with cardiac cycle in each heartbeat signal, and wherein the first level of the multi-level artificial neural network architecture is based on a time distributed convolutional 2-dimensional (2D) neural network level, and wherein the second level of the multi-level artificial neural network architecture is based on a time distributed Max Pooling 2D neural network level for downsampling the features;
generate a second dataset representing characteristics associated with the set of events by processing the first dataset at a third level and a fourth level of the multi-level artificial neural network architecture, wherein the third level is based on a flattening neural network level for converting the multi-dimensional data into a 1D tensor, and wherein the fourth level is based on a bidirectional Long Short-Term Memory (Bi-LSTM) neural network level for generating the second dataset;
compute a set of values associated with the set of events by processing the second dataset at a fifth level of the multi-level artificial neural network architecture, wherein the fifth level is based on a time distributed dense neural network level, and wherein the set of values represent time-based features of the pre-defined parameter; and compute a myocardial performance index based on the set of values, wherein the myocardial performance index is representative of the myocardial performance of the subject.

2. The system as claimed in claim 1, wherein the computation engine extracts the biomarker from micro-voltage digital datasets by:
   detecting the pre-defined parameter as a time-domain parameter; and
   converting the detected time-domain parameter to a frequency-domain parameter.

3. The system as claimed in claim 1, wherein the biomarker is representative of a heart rate present in micro-voltage digital datasets.

4. The system as claimed in claim 1, wherein the computation engine comprises a filtering unit executed by the processor and configured to extract the biomarker employing a bandpass frequency in a range of between 5 Hz and 15 Hz.

5. The system as claimed in claim 1, wherein the pre-defined parameter associated with the biomarker is representative of time-domain heartbeat signals.

6. The system as claimed in claim 2, wherein the computation engine comprises a heartbeat extraction unit executed by the processor and configured to convert the time-domain parameter to the frequency-domain parameter by dividing the time-domain parameter into short time-intervals prior to conversion of the time-domain parameter into an image representation in the frequency-domain, and wherein the short time-intervals are of 5 seconds.

7. The system as claimed in claim 6, wherein the image representation is representative of a spectrogram, and wherein the spectrogram represents the pre-defined parameter in a form of specific color variations.

8. The system as claimed in claim 2, wherein the time-domain parameter is converted to the frequency-domain parameter by the heartbeat extraction unit based on a Fourier Transform technique, and wherein the Fourier Transform technique is a Short-Term Fourier Transform (STFT) technique.

9. The system as claimed in claim 2, wherein the computation engine comprises a heartbeat processing unit executed by the processor and configured to determine the set of events by:
   a) processing the frequency-domain parameter at the first level of the multi-level artificial neural network architecture to extract features associated with the set of events;
   b) processing the features at the second level of the multi-level artificial neural network architecture;
   c) repeating steps a and b recursively at least three times to generate the first dataset in the form of the multi-dimensional data;
   d) processing the multi-dimensional data at the third level of the multi-level artificial neural network architecture; and
   e) processing the 1D tensor at the fourth level of the multi-level artificial neural network architecture.

10. The system as claimed in claim 1, wherein the set of values are computed by consecutively inserting multiple two concentric rectangular bounding boxes around the pre-determined parameter associated with the biomarker.

11. The system as claimed in claim 1, wherein the pre-defined parameter includes isovolumetric contraction time (IVCT) in a range of between 20 ms and 70 ms, isovolumetric relaxation time (IVRT) in a range of between 50 ms and 90 ms, left ventricular ejection time (LVET) in a range of between 150 ms and 350 ms and mitral closing to opening time (MOOT).

12. The system as claimed in claim 1, wherein the computation engine comprises a myocardial performance computation unit executed by the processor and configured to compute the myocardial performance index based on the second set of values.

13. A method for myocardial performance determination, the method comprising:
   generating, by a processor, a first dataset representing a set of events associated with a pre-defined parameter of a biomarker extracted from physiological parameters of a subject, wherein the physiological parameters are associated with ballistocardiographic (BCG) signals that are received from a sensor device that captures micro-vibrations from the subject in a contact-less manner, and wherein the set of events is determined by processing the pre-defined parameter at a first level and a second level of a multi-level artificial neural network architecture recursively for a pre-defined number of times to generate a multi-dimensional data, the set of events represent patterns associated with cardiac cycle in each heartbeat signal, and wherein the first level of the multi-level artificial neural network architecture is based on a time distributed convolutional 2-dimensional (2D) neural network level, and wherein the second level of the multi-level artificial neural network architecture is based on a time distributed Max Pooling 2D neural network level for downsampling the features;
   generating, by the processor, a second dataset representing characteristics associated with the set of events by processing the first dataset at a third level and a fourth level of the multi-level artificial neural network architecture, wherein the third level is based on a flattening neural network level for converting the multi-dimensional data into a 1D tensor, and wherein the fourth level is based on a bidirectional Long Short-Term Memory (Bi-LSTM) neural network level for generating the second dataset;
   computing, by the processor, a set of values associated with the set of events by processing the second dataset at a fifth level of the multi-level artificial neural network architecture, wherein the fifth level is based on a time distributed dense neural network level, and wherein the set of values represent time-based features of the pre-defined parameter; and
   computing, by the processor, a myocardial performance index based on the set of values, wherein the myocardial performance index is representative of the myocardial performance of the subject.

14. The method as claimed in claim 13, wherein the biomarker is extracted from micro-voltage digital datasets by detecting the pre-defined parameter as a time-domain parameter; and converting the detected time-domain parameter associated with the biomarker to a frequency-domain parameter.

15. The method as claimed in claim 13, wherein the biomarker is representative of a heart rate present in micro-voltage digital datasets.

16. The method as claimed in claim 13, wherein the biomarker is extracted based on a bandpass frequency in a range of between 5 Hz and 15 Hz.

17. The method as claimed in claim 13, wherein the pre-defined parameter associated with the biomarker is representative of time-domain heartbeat signals.

18. The method as claimed in claim 14, wherein the time-domain parameter is converted to the frequency-domain parameter by dividing the time-domain parameter into short time-intervals prior to conversion of the time-domain parameter into an image representation in the frequency-domain, and wherein the short time-intervals are of 5 seconds.

19. The method as claimed in claim 18, wherein the image representation is representative of a spectrogram, and wherein the spectrogram is representative of the pre-defined parameter in a form of specific color variations.

20. The method as claimed in claim 14, wherein the time-domain parameter is converted to the frequency-domain parameter based on a Fourier Transform technique, and wherein the Fourier Transform technique is a Short-Term Fourier Transform (STFT) technique.

21. The method as claimed in claim 14, wherein the set of events are determined by:
   a) processing the frequency-domain parameter at the first level of the multi-level artificial neural network architecture to extract features associated with the set of events;
   b) processing the features at the second level of the multi-level artificial neural network architecture;
   c) repeating steps a and b recursively at least three times to generate the first dataset in the form of a multi-dimensional data;
   d) processing the multi-dimensional data at the third level of the multi-level artificial neural network architecture; and
   e) processing the 1D tensor at the fourth level of the multi-level artificial neural network architecture.

22. The method as claimed in claim 13, wherein set of values are computed by consecutively inserting multiple two concentric rectangular bounding boxes around the pre-determined parameter associated with the biomarker.

23. The method as claimed in claim 13, wherein the pre-defined parameter including isovolumetric contraction time (IVCT) in a range of between 20 ms and 70 ms, isovolumetric relaxation time (IVRT) in a range of between 50 ms and 90 ms, left ventricular ejection time (LVET) in a range of between 150 ms and 350 ms and mitral closing to opening time (MOOT).

* * * * *